United States Patent
Jiang et al.

(10) Patent No.: US 7,632,231 B2
(45) Date of Patent: Dec. 15, 2009

(54) ULTRASONIC STRAIN IMAGING DEVICE AND METHOD PROVIDING PARALLEL DISPLACEMENT PROCESSING

(75) Inventors: Jingfeng Jiang, Madison, WI (US); Timothy Jon Hall, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 504 days.

(21) Appl. No.: 11/386,332

(22) Filed: Mar. 22, 2006

(65) Prior Publication Data

US 2007/0234806 A1   Oct. 11, 2007

(51) Int. Cl.
  *A61B 8/00* (2006.01)
(52) U.S. Cl. ............ 600/437; 600/444; 600/443; 600/439; 600/438; 600/446; 600/407; 73/597
(58) Field of Classification Search .......... 600/437, 600/443
  See application file for complete search history.

(56) References Cited

U.S. PATENT DOCUMENTS

| | | | |
|---|---|---|---|
| 6,277,074 B1 | 8/2001 | Chaturvedi et al. | |
| 6,508,768 B1 * | 1/2003 | Hall et al. | 600/443 |
| 6,863,655 B2 * | 3/2005 | Bjaerum et al. | 600/442 |
| 2003/0171672 A1 | 9/2003 | Varghese et al. | |
| 2004/0167403 A1 * | 8/2004 | Nightingale et al. | 600/437 |
| 2004/0215075 A1 | 10/2004 | Zagzebski | |
| 2004/0234113 A1 | 11/2004 | Miga | |

OTHER PUBLICATIONS

PCT International Search Report, ISA/USA, Mar. 31, 2008, US Commissioner for Patents, Alexandria, VA.

Fabian et al., Development of a Parallel Acquisition System for Ultrasound Research, Medical Imaging, 2001: Ultrasonic Imaging and Signal Processing, SPIE, vol. 4325, p. 54-62, 2001.

* cited by examiner

*Primary Examiner*—Long V Le
*Assistant Examiner*—Nigel Fontenot
(74) *Attorney, Agent, or Firm*—Boyle Fredrickson, S.C.

(57) ABSTRACT

A device for ultrasonic strain imaging computes displacement of tissue between a pre-deformation and post-deformation data set along columns to provide for independent calculations that may be parallelized for multiprocessor systems.

25 Claims, 5 Drawing Sheets

ULTRASONIC STRAIN IMAGING DEVICE AND METHOD PROVIDING PARALLEL DISPLACEMENT PROCESSING

STATEMENT REGARDING FEDERALLY SPONSORED RESEARCH

This invention was made with United States government support awarded by the following agencies:
NIH CA100373
The United States government has certain rights in this invention.

CROSS-REFERENCE TO RELATED APPLICATIONS

- - -

BACKGROUND OF THE INVENTION

The present invention relates to ultrasonic imaging and, in particular, to an improved method and apparatus for calculating material displacement used to produce elasticity images including local strain, modulus and Poison' ratio images.

Ultrasonic elasticity imaging produces an image showing the elasticity of the material being measured. When used in medicine, elasticity imaging is analogous to palpation by a physician, that is, the pressing of tissue by the physician to feel differences in elasticity of underlying structures.

In a common form of elasticity imaging, two separate ultrasonic images are obtained, the first image with tissue in an undeformed state relative to the second image ("initial, pre-deformation") and the second image with the tissue in a deformed state ("post deformation"). The two images are analyzed to deduce the amount of displacement of the tissue at corresponding areas within the images. One realization of tissue elasticity information is the local strain, i.e. the gradient in the displacement computed at many points over the image provides an indication of the tissue elasticity at those points. The general principles of elasticity imaging and techniques for determining displacement of the tissue between two ultrasonic images are described in detail in U.S. Pat. No. 6,508,768, hereby incorporated by reference.

An important aspect of processing the pre-deformation and post-deformation ultrasonic images to deduce the displacement of tissue elements is identifying corresponding points in the two images. This is normally accomplished by identifying each point in the pre-deformation image and establishing a region of points (kernel) surrounding that identified point. This kernel is then moved within a search window within the post-deformation image to identify the location within the search window providing the best match between the points within the kernel and a corresponding kernel in the post-deformation image. Note that both the kernel and the search window are not limited to be two-dimensional. The kernel size is selected to be large enough to ensure reliable matches between corresponding points in the pre-deformation and post-deformation images, but small enough to provide for fast calculation of matching and high-resolution strain images.

The determination of a best match can be according to one of a number of different statistical techniques, for example, by computing the sum of the square of the differences between the image values of corresponding points in the kernels of the undeformed and the deformed images.

Normally the size of the search window must be great enough to accommodate likely tissue displacements between the pre-deformation and post-deformation images, but limited to manage the computational burden of matching points with each other and to reduce the chance of possible false matches that violate a priori assumptions about limited mobility of a continuum reacting to external mechanical stimuli. Additional computational speed may be provided by offsetting the location of the search window within the post-deformation data, and further limiting its size, based on previously computed displacements of nearby tissue. This approach also relies on assumptions of continuity among displacement values resulting from bounded elasticity of a known imaged material.

Commonly, when elasticity imaging is used in a medical setting, an ultrasonic transducer is used both to acquire imaging data and to provide manual deformation to the tissue. This results in an axial deformation aligned generally with the ultrasonic beam axis of the transducer in which the calculated displacement with respect to the contact of the transducer and tissue will increase with distance from the transducer.

In such systems, displacements are normally calculated on a row-by-row basis, with rows extending through the tissue generally perpendicularly to the axis of the ultrasonic beam. The computation of displacements starts at a row closest to the transducer and having lowest expected displacements, thereby limiting the necessary area of the search windows. As each row is calculated, the displacements at that row may be corrected by comparisons among row elements to remove erroneous points in light of assumptions about limits of shearing in the tissue. Once a given row is complete, the next row further away from the transducer may be computed, again using search windows sized and located using information about previously determined displacements from the previous row. When all rows are completed, an elastic strain image may be produced. Other elastic parameters such as modulus and Poison's ratio can also be estimated by the calculated displacement function.

Desirably, the time and computationally intensive matching of the kernels to data of the post-deformation data could be divided among multiple processors to be executed in parallel for improved real-time elasticity imaging. Unfortunately, each successive row of displacement data is highly dependent on the earlier rows, particularly for refining the size and location of the search windows. Further, independent processing of the rows in small groups associated with different processors raises a problem of "collisions" in which errors in the calculations of individual rows are propagated within the group to produce discontinuities when the groups meet at interfaces between the groups.

For these reasons, improvements in the execution speed of the calculation of elasticity images, highly desirable to guide the operator in manual deformation of the tissue, must wait for incremental improvements in processor speed as new processors are introduced into medical equipment.

SUMMARY OF THE INVENTION

The present inventors have recognized that parallel processing can be practical in elasticity imaging by the simple expedient of computing displacements along columns of tissue rather than on a row-by-row basis. Note that a column is defined as a data segment generally parallel to the axis of the ultrasonic beam. The early calculations necessary for each column remain near the transducer allowing efficient search windows to be used, and previous column data allows continued refinement of the window sizes and locations as with the row-by-row approach. The computation of displacement data in two columns progressing outward from a pre-computed center column substantially eliminates the problem of collisions. Additional time taken in the determination of displacement for the central column, which need be done only once, benefits the remaining column calculations.

Specifically then, the present invention provides a method of ultrasound strain imaging in which a first and second ultrasonic echo data are acquired with an axial ultrasonic beam passing through a material, the material subject to a first and second state of axial deformation. The echo data provides data points along axial columns and lateral rows of one or more image planes. Displacements of elements of the material are determined by comparing data points of the first and second echo data on a column-by-column basis meaning that a determination of displacement of data points of a first column is substantially complete before determination of displacement for data points of at least one second column is substantially begun. A strain image is produced using the determination of displacement of the first and second ultrasound echo data.

It is thus one object of at least one embodiment of the invention to perform the calculations of displacement along the axis of the ultrasound beam thereby aggregating the data that is dependent on a particular ultrasonic path and allowing simultaneous or parallel processing of other column data independently of the given column data. Unlike the computation in rows which efficiently must occur in sequence, computation along columns may be performed largely independently.

The determination of displacement elements for the second column may use displacement calculated in the first column to limit a comparison of data points in the first and second ultrasound echo data in determination of the displacement of the elements of the second column.

Thus it is another object of at least one embodiment of the invention to allow sequential, independently processed columns to nevertheless serve to inform the efficient processing of later columns to the extent that both parallel and serial processing of columns can be expected to occur.

A second and third column on opposite sides of the first column may be computed in parallel.

Thus it is an object of at least one embodiment of the invention to employ a computational sequence that eliminates collisions between computations of independent columns.

The determination of displacement of elements in the first column may locate in the middle of the ultrasound echo data where the ultrasound transducer is in good contact with the material.

It is thus another object of at least one embodiment of the invention to acquire data in a location that induces less undesirable motion (i.e. lateral and out-of-plane motion) and that is beneficial for balancing loads among two computing processors.

The determination of displacement of elements in the first column may use more complex processing, for example, by comparing data points in the first and second ultrasound echo data sampled at different frequencies from coarse to fine for more robust estimates. Statistical methods requiring more computing time (e.g. Viterbi algorithm (IEEE Trans. Information Theory, 1967) based on the Hidden Markov Model (Grimmett and Stirzaker, "Probability and random processes", 2nd ed., Oxford University Press, 1992) may also be used in determining displacement elements in the first column for more robust estimates.

Thus it is an object of at least one embodiment of the invention to effectively allocate additional computational resources to the first column estimation that may have the greatest interest.

The determination of displacement of elements in the first column may compare data points in the first and second ultrasound echo data over a larger spatial range than the determination of displacement of elements in the second column.

Thus it is an object of at least one embodiment of the invention to allow a first column to use larger search windows at greater computational expense than later columns which may make use of the displacement information derived from the first column.

The determination of displacement of elements in the first column may also or alternatively compare a larger set of data points in the first and second ultrasound echo data than the determination of displacement of elements in the second column.

Thus it is another object of at least one embodiment of the invention to allow variations in kernel sizes and/or search windows among columns according to the value of the column in guiding the search windows in other columns.

The larger set of data points for the first column may include data from multiple columns to compare their consistency, looking for favorable evidence that the displacement estimates are accurate given the knowledge of motion continuity described above. The approach is consistent with Bayesian confirmation theory (Fitelson, B., The Plurality of Bayesian Measures of Confirmation and the Problem of Measure Sensitivity. *Philosophy of Science* 66 (Proceedings), S362-S378, 1999 or Earman J, "Bayes or bust?: a critical examination of Bayesian confirmation theory", MIT Press, 1992).

It is thus another object of at least one embodiment of the invention to provide improved robustness to a first guiding column by looking at spatially independent columns of data.

The method may include the step of correcting displacement in the first and/or second column by a statistical analysis of displacement within the same first and second column.

Thus it is another object of at least one embodiment of the invention to provide for regularization that does not interfere with parallel processing of columns by limiting the regularization process to column data.

The process may include the step of determining a global displacement of elements of the material representing an average displacement over many elements, and the global displacement may be used to limit a comparison of data points in the first and second ultrasound echo data in the determination of displacement.

It is thus another object of at least one embodiment of the invention to provide efficient search windows in the initial columns.

The global displacement may be obtained from a row of elements displaced from the row close to an origination of the ultrasound beam. The row location is selected to be close enough to the contact surface between the ultrasound transducer and the object being imaged to ensure a small search region is sufficient, but deep enough that the estimated motion is representative of the average global tissue motion in the region.

It is thus another object of at least one embodiment of the invention to provide a global displacement value that is usable over the full width of the image.

These particular objects and advantages may apply to only some embodiments falling within the claims, and thus do not define the scope of the invention.

DETAILED DESCRIPTION OF THE PREFERRED EMBODIMENT

Figure 1:
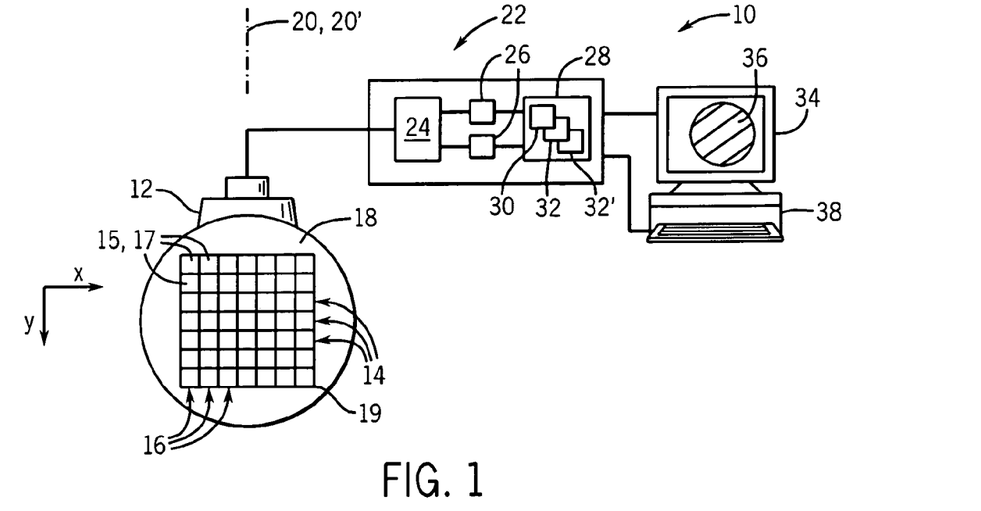
FIG. 1 is a simplified representation of an ultrasound imaging machine suitable for practice of the present invention showing an ultrasonic transducer for collecting of rows and columns of ultrasound data and for manually deforming tissue of object, and showing a multiprocessor computer for processing the ultrasound data according to a stored program to produce an ultrasonic strain image on a display device.

Referring now to FIG. 1, an elasticity imaging machine 10 of the present invention includes an ultrasonic array transducer 12 that may transmit and receive ultrasonic signals along a propagation axis 20 to acquire ultrasonic echo data points 15 at corresponding volume elements 17 throughout a region of interest 19 in the tissue of an object 18.

The echo data points 15 and the volume elements 17 may be identified by logical rows 14 and columns 16, wherein the rows 14 are generally lines of echo data points 15 or volume elements 17 extending perpendicularly to the propagation axis 20, and the columns 16 are generally lines of echo data points 15 or volume elements 17 extending parallel to the propagation axis 20. These terms should be understood generally to describe data acquired through a variety of ultrasonic acquisition geometries including those which provide for fan beams of ultrasound and the like, and therefore not be limited to strictly rectilinear rows and columns.

In addition to transmitting and receiving ultrasonic signals along the propagation axis 20, the transducer 12 may also provide a source of deformation along deformation axis 20' generally aligned with a propagation axis 20 of ultrasound from the transducer 12.

The transducer 12 communicates with a processing unit 22 that both provides waveform data to the transducer 12 used to control the ultrasonic beam and collects the ultrasonic echo signals (radio-frequency data). As is understood in the art, processing unit 22 provides for necessary interface electronics 24 that may sample the ultrasonic echo signals to produce the echo data points 15. The interface electronics 24 operates under the control of one or more processors 26 communicating with a memory 28, the latter which may store the echo data points identified to rows 14 and columns 16 to form data sets 32 of echo data points 15 as will be described.

Generally, the processors 26 may execute a stored program 30 contained in memory 28 as will also be described below. The processors 26 also may communicate with an output screen 34 on which may be displayed a strain image 36 and with a keyboard or other input device 38 for controlling the processing unit 22 and allowing for user input as will be understood to those of skill in the art.

Figure 2:
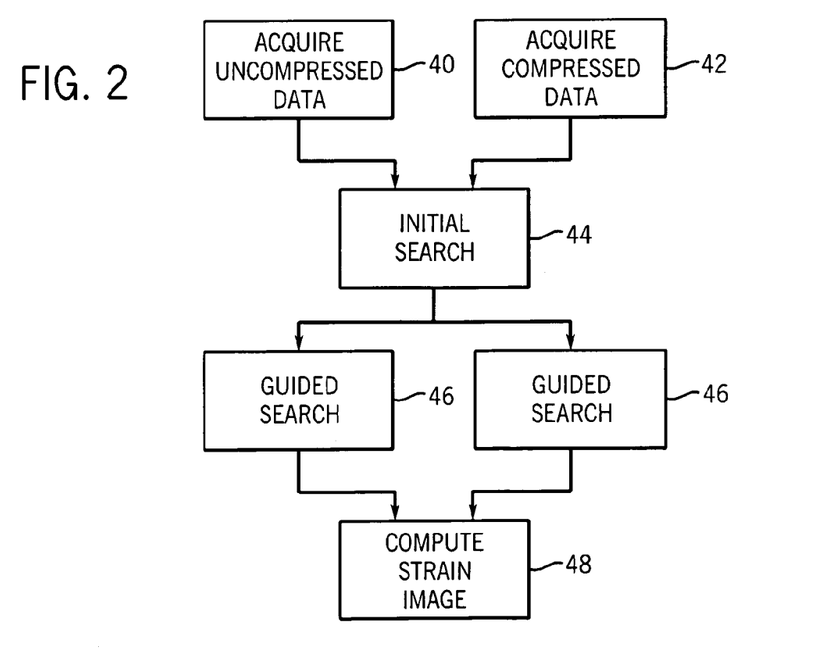
FIG. 2 is a flow chart of the principal steps of the present invention in an initial search stage for computing global displacement and displacement of a central column, and subsequent guided search stages that may be executed in parallel by the multiple processors of the computer of FIG. 1.

Referring now also to FIG. 2, per the present invention, the program 30 provides for the acquisition of two data sets 32 from the echo data points 15: a pre-deformation data set 32 indicated by process block 40, and a post-deformation data set indicated by process block 42. Generally the pre-deformation data set 32 will be acquired with the transducer 12 resting lightly on the object 18 and the post-deformation data set 32' will be acquired with the transducer 12 pressed inward to provide an approximately 1 to 5 percent axial strain of the tissue of the object 18. These two data sets may be differentiated by input by the operator through input device 38 or may be extracted automatically by a switch on the transducer 12 or other techniques.

Once the pre-deformation data set 32 and post-deformation data set 32' are obtained, the data of the two data sets 32 are compared in an initial search indicated by process block 44. Generally during this initial search, a single processor 26 analyzes the data to obtain a global displacement value for the tissue of a region of interest 19 caused by the deformation with the transducer 12. The global displacement value is then used to guide a determination of displacement along a central column 16 of data as will be described.

At subsequent process block 46, guided searches of the data sets 32 may be conducted independently by the two processors 26 in which the displacement values determined in the initial search of process block 44 is used to determine displacement data for other columns 16 of the region of interest 19.

As indicated by process block 48, upon completion of the displacement calculation of the guided searches, displacement determinations over the entire region of interest 19 are reconstructed into a computed strain, modulus or Poison's ratio image.

Figure 3:
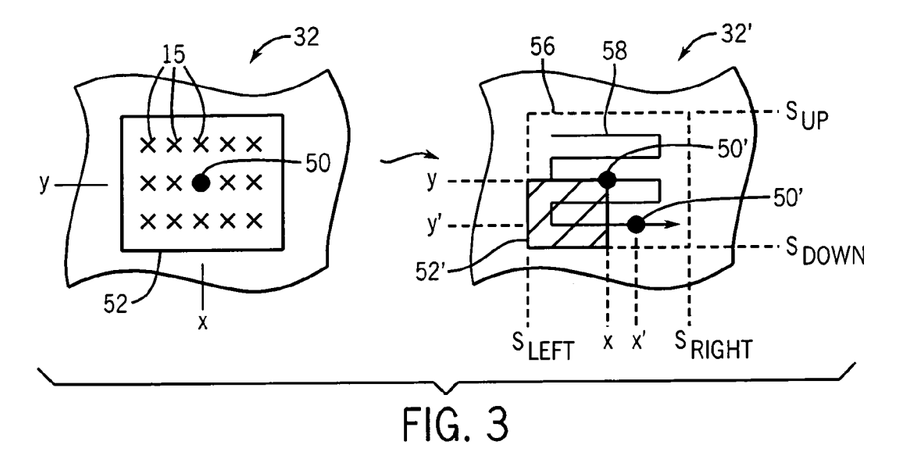
FIG. 3 is a fragmentary representation of selected rows and columns of ultrasound data collected in FIG. 1 of a pre-deformation image and a post-deformation image showing a block matching of data of a kernel within a search window to deduce tissue displacement.

Referring now to FIG. 3, the process of analyzing the pre-deformation data set 32 against the post-deformation data set 32' requires that the spatial location (coordinates x and y) of each base point 50 (of the echo data points 15) in the pre-deformation data set 32 be identified to a moved base point 50' of echo data points 15' (coordinates x' and y') in the post-deformation data set 32'. To do this, a kernel 52 is defined embracing the base point 50, and a set of adjacent echo data points 15 within the kernel 52. The data points 15 of this kernel 52 are compared to the corresponding data points 15' of a correspondingly sized kernel 52' in the post-deformation data set 32' as kernel 52' is moved over a range of locations within a search window 56 in the post-deformation data set 32'.

For example, the kernel 52' may be moved to a variety of locations in a regular search pattern 58 within the search window 56 and the degree of matching between corresponding echo data points 15 and 15' at each location may be quantified through a variety of well known techniques, for example, a sum of squared differences (SSD), as will be described, at each location. The location of the kernel 52' with the best match defines a matching base point 50' corresponding to base point 50, the difference between the base point 50 and matching base point 50' defining the displacement of the tissue at base point 50 with deformation.

The computational burden of this process will depend on the number of echo data points 15 within the kernel 52 and 52' at which differences are calculated, and the size of the search window 56 through which kernel 52' is moved. Generally, the former quantity is determined by the desired resolution and accuracy of the image, and therefore, the greatest potential for computational savings will be in reducing the size of the search window 56 to the extent possible based on prior knowledge about the probable location of each matching base point 50'.

Figure 4:
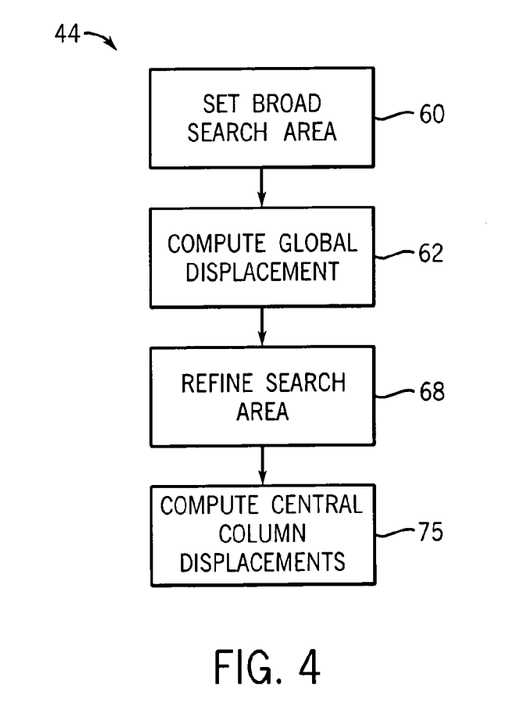
FIG. 4 is a flow chart showing sub-steps within the initial search stage of FIG. 2.

Referring now also to FIG. 4, accordingly in the initial search step of process block 44, when very little knowledge about the tissue displacement has been obtained, a large search window 56 is defined at process block 60. In a preferred embodiment, the upper and lower bounds of the search window 56 (e.g., $S_{up}$ and $S_{down}$) may be set equal to a fixed percentage of the total number of samples in each column 16 of the region of interest 19 empirically determined to represent the maximum likely displacement of soft tissue (e.g. about 5 percent). A similar right and left boundary $S_{right}$ and $S_{left}$ may be set to a fixed multiple of the width of the ultrasonic beam provided by the transducer (e.g., four) empirically determined to approximate the maximum expected lateral strain. Generally, this broad search window 56 will be such as to ensure accurate matching of kernel 52 and kernel 52' without optimization for reduced computational time.

Figure 5:
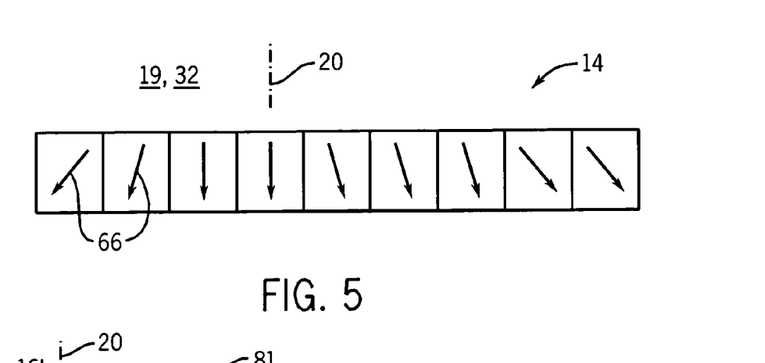
FIG. 5 is a representation of a displacement vector computed on one row of ultrasound data of FIG. 1 to compute a global displacement.

At process block 62 shown in FIG. 4, a global displacement is computed by examining a single row 14 of data (shown in FIG. 5) located near the top of the region of interest 19 and the data set 32. Typically, for example, if 1000 sampled data points 15 are obtained in a given column 16, the initial row 14 will be at row 200. The location of this small region of interest is chosen to ensure that the motion in a small search region is representative of the average net axial motion of the full region of interest being studied. A block matching performed using the broad search, is defined in process block 60 to produce a set of displacement vectors 66 for representative volume elements 17 across the row 14. The vectors 66 are averaged to provide a global displacement value 70 (shown in FIG. 8) indicating the general displacement of the tissue under deformation that incorporates data from the right and left sides of the region of interest 19, Thus, this global displacement value 70 is intended to accurately reflect the average displacement of the tissue without requiring an extensive computation of a large number of displacement values.

Figure 8:
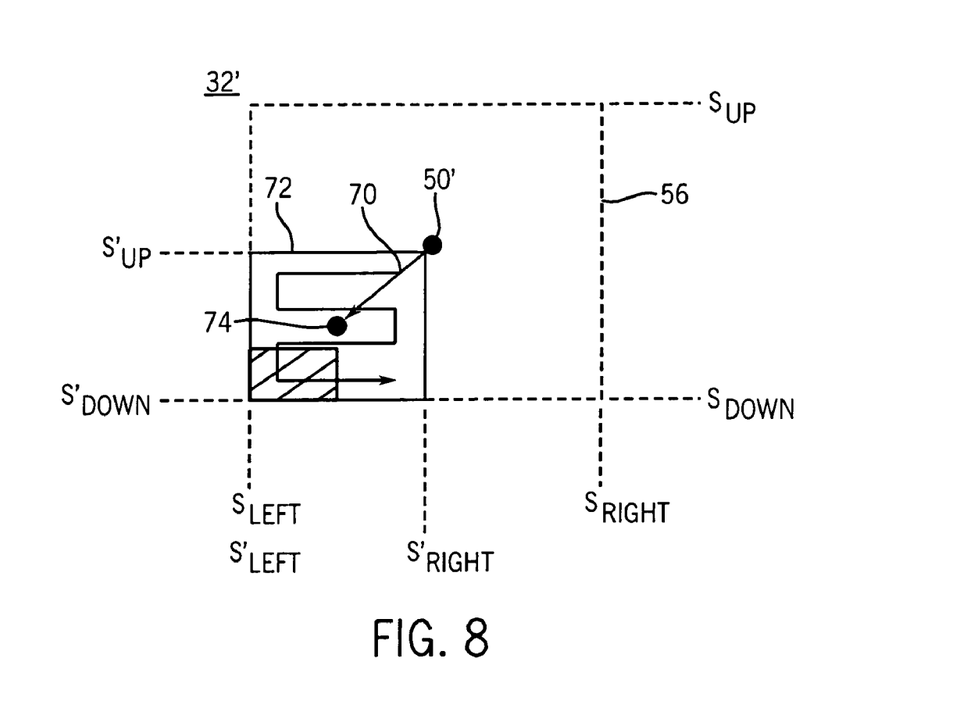
FIG. 8 is an example of the block matching process of FIG. 3 using displacement data from a previous column to improve the search pattern for matching.

Referring now to FIGS. 4 and 8 per process block 68, the global displacement value 70 may be used to refine the search windows 56 of process block 60. In particular, the global displacement value 70 locates a new window center point 74 removed from base point 50 in the post-deformation data set 32, with a corresponding reduced search window 72 centered on window center point 74. Generally the reduced search window 72 will have new left and right boundaries $S'_{left}$ and $S'_{right}$ and $S'_{up}$ and $S'_{down}$, reflecting an empirically determined reduction of the necessary search area given knowledge of the global displacement of the tissue.

Figure 6:
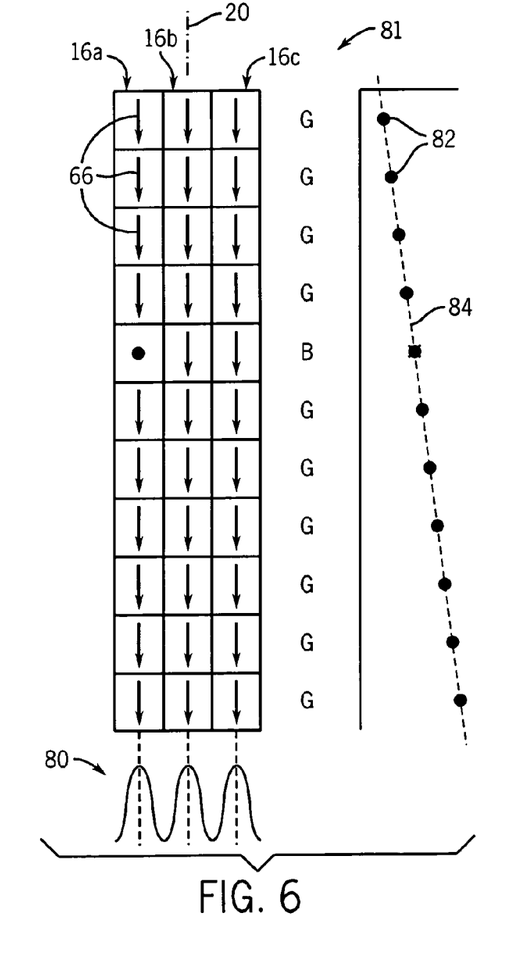
FIG. 6 is a representation similar to FIG. 5 of three columns of vector data used to establish guiding displacement values for subsequent columns of data showing a statistical anomaly detection process relying only on intra-column data.

Referring now to FIGS. 4 and 6, finally at process block 75, the reduced search window 72, determined from the global displacement value 70, is used to compute displacement values of three columns 16a, 16b, and 16c preferably centered in the region of interest 19. Each of the columns 16a, 16b and 16c generally represent data obtained with different ultrasonic beams, or in other words, data separated by a cross-axial distance great enough that correlation 80 between the displacements calculated from the data of the columns 16a, 16b and 16c caused by beam overlap is relatively low and the displacements derived from the data of the three columns 16a through 16c is substantially independent.

Displacement vectors 66 are determined for each of these columns using the block matching with the reduced search window 72 described above. Then, a correction process 100 is undertaken in which the displacement vectors 66 on each row of the columns 16a through 16c are compared to see that they "track" each other (e.g. provide a vector difference between any two vectors 66) to less than a predetermined empirically defined threshold. If the displacement values among the columns 16a through 16c track, the data of the columns 16a through 16c is considered good. This determination is indicated in FIG. 6 by a letter G in column 81 aligned with the given row. If the displacement values do not so track, (indicated in FIG. 6 by a letter B aligned with the given row) the outlying vector 66 is replaced with a value interpolated from the remaining vectors 66 of that column, as follows. Each of the good displacement vectors (indicated by letter G) of the columns 16a through 16c (shown in FIG. 6 for only a single column 16a and a single vector dimension 82) may be fit to a curve 84 used to filter the displacement vectors so determined. This correction process 100 may be performed independently for each of the columns 16 and does not require reference to any other column 16. Alternatively, at the process block 75, the central column of displacements can be determined by a dynamic programming method (e.g. Viterbi algorithm, A. J. Vertibi, IEEE Trans. Information Theory, 1967) using a cost function $$C = \int\int_\Omega (\gamma E_c + E_s),$$

where $\gamma$ is an adaptively chosen scale factor, $E_c$ is the penalty from speckle de-correlation and $E_s$ is the penalty from losing data continuity (i.e. displacement differences or derivatives). Referring still to the process block 75, to reduce the search region for the central column of displacements, the entire column can be segmented into smaller regions (20-30 displacement vectors). Then, the displacements estimated from a shallow depth can be used to offset the location of the search window for deeper segments, limiting the size of search region and therefore computing resources. Alternatively, the estimation of central column of displacements may be performed in the first and second ultrasound echo data sampled at different frequencies from coarse to fine for more robust estimates without losing computational efficiency.

Once this process is complete, the displacement vector 66 among individual rows of the columns 16a, 16b, and 16c are averaged to produce a single column of robust displacement data.

It will be understood that this computation of displacement data for the central column 16 as part of the initial search of process block 44 of FIG. 2, is relatively time consuming based on the size of the search window (even reduced search window 72), if it is executed as a single sequential thread in the simplest implementation. This data, however, may then be used for the parallel guided searches of process blocks 46 shown in FIG. 2 which comprise the bulk of the displacement calculations. Accordingly, the extra time taken for the initial search of process block 44 provides a proportionately low influence on the total computation time required to generate an elasticity image. However, it is worth noting that the initial search of process block of FIG. 2 can be computed in parallel, as described below.

Figure 7:
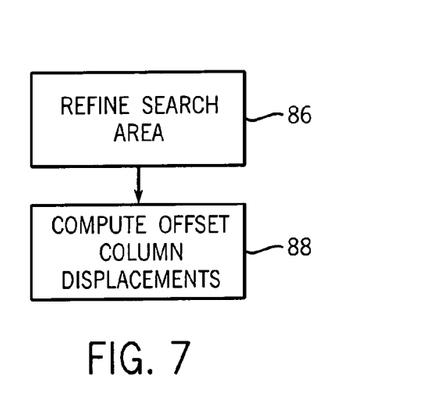
FIG. 7 is a flow chart showing the sub-steps within the guided searches of FIG. 2 as may be executed in parallel by the processors of FIG. 1.
Figure 9:
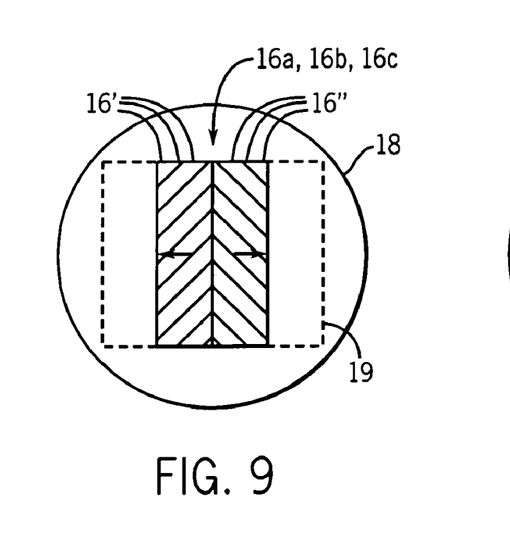
FIG. 9 is a representation of the ultrasound data of FIG. 1 showing a computational sequence providing parallel outward processing of columns with two processors.

Referring now to FIGS. 2, 7, and 9, parallel processing of the data sets 32 may now be performed in the guided searches of process blocks 46 using new columns 16' and 16" beginning immediately to the left and right of the columns 16a, 16b and 16c. As indicated by process block 86 of FIG. 7, the computation of displacements for these new columns 16 may use the computed displacements of the combined columns 16a and 16c to further refine the search window 56 using the same process described above with respect to FIG. 8 where the displacement value 70 is that derived from the column 16a, 16b and 16c.

As shown in FIG. 9, after the displacement values for each column 16' to the left of the columns 16a, 16b and 16c is completed by a first processor 26 at process block 88 of FIG. 7, computation for the next column 16' to the left is begun. Likewise after the displacement values for each column 16" to the right of the columns 16a, 16b and 16c is completed by a second processor 26 at process block 88 of FIG. 7, computation for the next column 16" to the right is begun. The computations for each column 16' and 16" uses the calculated displacement vectors of the previously computed column 16 only as a displacement value 70 to inform and refine the search for process block 86. The displacement values computed for each of these new columns may be separately filtered using the curve fitting techniques as described above or other filtering techniques relying solely on the data of the given column so as to maintain that ability to process each column 16', 16" on a separate processor as an independently executing thread.

This process is repeated until displacement values are computed over the entire region of interest 19 at which time computed strain images are performed as has been described with respect to process block 48 of FIG. 2.

It will be understood, referring to FIG. 9, that because the computation of displacements proceeds column-by-column outward from the center of the region of interest 19, there is no possibility of collisions in which inconsistent values of displacements are computed for adjacent columns 16. Nevertheless, displacement calculations may be performed by at least two processors 26 operating simultaneously in parallel.

Figure 10:
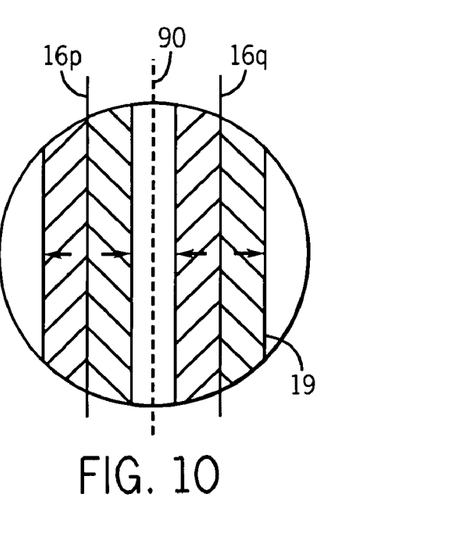
FIG. 10 is a figure similar to that of FIG. 9 showing a possible computational process using four processors.

Referring to FIG. 10, while limiting the calculation to two threads avoids a collision problem, the present invention does not preclude the possibility of more than two processors 26 computing displacements, for example, starting with columns 16p and 16q symmetrically displaced from a central column 90 centered in the region of interest 19, and proceeding outward from each of those columns. This approach risks a collision at the center column 90, but is believed that any discontinuities will be small based on the robust nature of the calculation process and may be corrected, for example, by filtering techniques.

Figure 11:
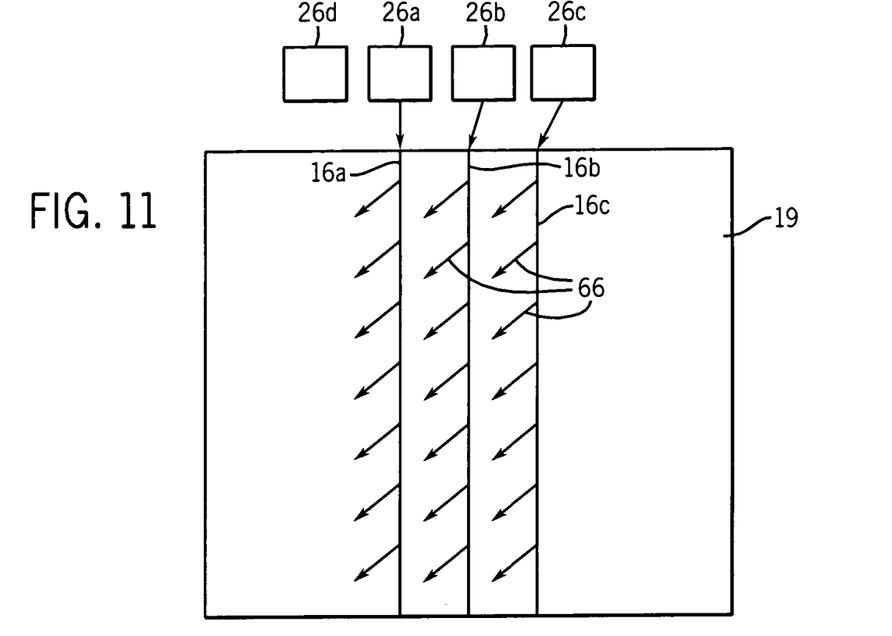
FIG. 11 is a figure similar to that of FIG. 10 showing an alternative computational process for using four processors for an initial search.

The parallelism of this invention described above is not limited to dual processors. An example of using four processors is given here and this scheme can also avoid the collision problem. Referring to FIGS. 6 and 11, also at process block 75, computing displacement values of three columns 16a, 16b and 16c with the reduced search window 72 can be completed using four different processors 26a-d. Processors 26a-c are responsible for estimating displacement vectors 66 for three columns 16a, 16b and 16c independently, while the fourth processor 26d will handle the correction process 100 in parallel, as described before.

Once the correction process 100 is done by the fourth processor 26d, the fourth processor 26d will also provide a single column of robust initial displacement data by averaging individual rows of the columns 16a, 16b and 16c obtained from the processors 26a-c, respectively.

It will be understood that this computation of displacement data for the central column 16 as part of the initial search of process block 44 of FIG. 2 becomes more efficient by adopting this scheme.

Figure 12:
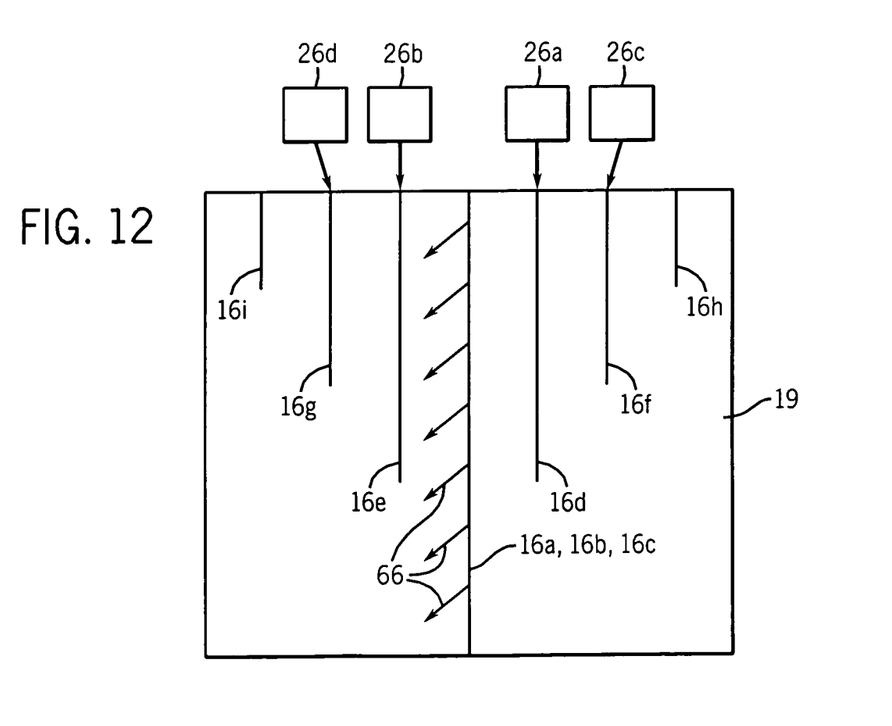
FIG. 12 is a figure similar to that of FIG. 11 showing an alternative computational process for using four processors for a guided search.

Referring now to FIGS. 2, 9, and 12, parallel processing of the data sets 32 may now be performed in the guided searches of process block 46 beginning immediately to the left and right of the column 16 (i.e. combined columns of 16a, 16b and 16c) with the four processors 26a-26d. As indicated in FIG. 12, the processors 26a and 26b start to compute new columns of 16e and 16d, respectively, immediately after the completion of the initial search (process block 44 of FIG. 2). After a substantial portion (e.g. ⅓) of displacement vectors 66 in these new columns of 16e and 16d is completed, new columns of 16f and 16g may be started using processors 26c and 26d, respectively. After the completion of columns of 16e and 16d, the processors 26a and 26d may start to process new columns of 16h and 16i using the information from the estimated portion of 16f and 16g, respectively. This process is repeated until displacement values are computed over the entire region of interest 19.

The overlapping parallel processing avoids the collision problems that may occur in the embodiment of FIG. 10

This invention described above is also not limited to two-dimensional motion tracking.

It is specifically intended that the present invention not be limited to the embodiments and illustrations contained herein, but include modified forms of those embodiments including portions of the embodiments and combinations of elements of different embodiments as come within the scope of the following claims.

We claim:

1. A method of ultrasound strain imaging comprising the steps of:
   (a) acquiring first and second ultrasound echo data with an axial ultrasonic beam passing through a material subject to a first and second state of axial deformation, respectively, the echo data corresponding to a plurality of volume elements identified by a plurality of columns extending substantially parallel to an axis of propagation of the beam and a plurality of rows extending substantially perpendicular to the axis of propagation of the beam; and
   (b) calculating a displacement vector for at least one of the plurality of volume elements to determine displacement of the material by comparing the first and second echo data on a column-by-column basis, wherein a determination of displacement vectors for the volume elements of a first column is substantially complete before a determination of displacement vectors for the volume elements of at least one second column to be determined is substantially begun; and
   (c) producing elasticity images of the material using determinations of displacement between the first and second ultrasound echo data.

2. The method of claim 1 wherein the elasticity imaging provides elasticity expressed as at least one of local strain, modulus and Poison's ratio.

3. The method of claim 1 wherein determination of displacement vectors for the second column uses displacement vectors calculated in the first column to limit a comparison of volume elements between the first and second ultrasound echo data in determination of displacement of the material in the second column.

4. The method of claim 1 wherein a determination of displacement vectors in the first column is substantially complete before a determination of displacement vectors in the second and a third column is substantially begun, and wherein the second and third columns are on opposite sides of the first column, and determination of displacement vectors in the second and third columns is substantially performed in parallel.

5. The method of claim 1 wherein determination of displacement vectors in the first column compares volume elements in the first and second ultrasound echo data over a larger spatial range than the determination of displacement vectors in the second column.

6. The method of claim 1 wherein the determination of displacement vectors in the first column is located in ultrasound echo data corresponding to a middle of the material measured by the ultrasonic echo data set.

7. The method of claim 1 wherein determination of displacement vectors in the first column compares volume elements between the first and second ultrasound echo data using methods that require relatively greater computation time than methods for the determination of displacement vectors in the second and subsequential columns.

8. The method of claim 1 wherein determination of displacement vectors in the first column compares a larger set of volume elements between the first and second ultrasound echo data than the determination of displacement vectors in the second column.

9. The method of claim 8 wherein the larger set of volume elements includes volume elements of multiple columns of data and also contains volume elements from one or more image planes.

10. The method of claim 1 further including the step of correcting determined displacement vectors in a column-by-column basis by statistical analysis of displacement only within the same column of displacement vectors.

11. The method of claim 1 further including the step, before step (b), of determining a global displacement of the material representing an average displacement over many volume elements;
wherein step (b) uses the global displacement to limit a comparison of the first and second ultrasound echo data in the determination of displacement.

12. A method of ultrasound strain imaging comprising the steps of:
(a) acquiring first and second ultrasound echo data with an axial ultrasonic beam passing through a material subject to a first and second state of axial deformation, respectively, the echo data corresponding to a plurality of volume elements identified by a plurality of columns extending substantially parallel to an axis of propagation of the beam and a plurality of rows extending substantially perpendicular to the axis of propagation of the beam;
(b) determining displacement of the material by independently comparing the first and second echo data in a first and second column simultaneously to determine a displacement vector for each of the volume elements in the first and second columns; and
(c) producing elasticity images of the material using determinations of displacement between the first and second ultrasound echo data.

13. The method of claim 12 wherein the determination of displacement vectors of volume elements of the first and second columns employs information derived from a third column.

14. The method of claim 12 including the step of repeating step (b) with new first and second columns adjacent and outside of earlier first and second columns.

15. The method of claim 12 wherein determination of displacement vectors of volume elements of the first and second columns uses displacement vectors of volume elements calculated in a third column to limit a spatial range of comparison of volume elements between the first and second ultrasound echo data in the determination of displacement vectors of volume elements in the first and second columns.

16. The method of claim 15 wherein determination of displacement vectors of volume elements in the third column compares volume elements between the first and second ultrasound echo data over a larger spatial range than the determination of displacement vectors of volume elements in the first and second column.

17. The method of claim 15 wherein determination of displacement vectors of volume elements in the third column compares a larger set of volume elements between the first and second ultrasound echo data than the determination of displacement vectors of volume elements in the first and second column.

18. The method of claim 17 wherein the larger set of volume elements includes volume elements of multiple columns and also contains volume elements of one or more image planes.

19. The method of claim 15 wherein the first and second columns are on opposite sides of the third column.

20. The method of claim 15 wherein determination of displacement vectors in the first and second columns uses a limited spatial range in the comparison of the first and second ultrasound echo data based on determinations of displacement vectors of volume elements in previous adjacent columns.

21. The method of claim 15 further including the step of collecting displacement vectors along the first and second column by statistical analysis of displacement limited to volume elements of each column.

22. The method of claim 15 further including the step before step (b) of determining a global displacement of the material, representing an average displacement over many volume elements;
and wherein step (b) uses the global displacement to limit a comparison of the first and second ultrasound echo data in the determination of displacement.

23. The method of claim 22 wherein the global displacement is obtained from a row of elements displaced from a row closest to an origination of the ultrasonic beam.

24. An ultrasound strain imaging machine comprising:
(a) a transducer assembly producing an axial ultrasonic beam through a material and acquiring an echo signal from that material;
(b) an electronic computing unit including:
(i) at least a first and second computing processor;
(ii) a stored program executable on the electronic computing unit to execute:
(1) acquiring a first and second ultrasound echo data with the transducer assembly corresponding to a first and second state of axial deformation of the material, respectively, the echo data corresponding to a plurality of volume elements identified by a plurality of columns extending substantially parallel to an axis of propagation of the beam and a plurality of rows extending substantially perpendicular to the axis of propagation of the beam; and (2) calculating a displacement vector for at least one of the plurality of volume elements to determine displacement of the material by comparing the first and second echo data substantially simultaneously in a first column using the first processor and a second column using the second processor; and (3) producing a elasticity information image of the material from the determined displacements.

25. The ultrasound strain imaging machine of claim 24 further including a third computing processor, and wherein the electronic computing unit further executes the stored program to determine displacement of the material by comparing the first and second echo data substantially simultaneously in a first column using the first processor, a second column using the second processor, and a third column using the third processor.

* * * * *